United States Patent [19]

Amati

[11] Patent Number: 4,778,476
[45] Date of Patent: Oct. 18, 1988

[54] USE OF PHOSPHORIC ACID PARTIAL ESTERS IN FATTING OF TANNED LEATHER

[75] Inventor: Werner Amati, Hersberg, Switzerland

[73] Assignee: Sandoz Ltd., Basel, Switzerland

[21] Appl. No.: 885,022

[22] Filed: Jul. 10, 1986

Related U.S. Application Data

[63] Continuation of Ser. No. 722,312, Apr. 11, 1985, abandoned, which is a continuation of Ser. No. 410,663, Aug. 23, 1982, abandoned.

[51] Int. Cl.$^4$ ............................................. C14C 9/02
[52] U.S. Cl. ................................... 8/94.23; 8/94.1 P; 427/337; 427/389
[58] Field of Search ................. 8/94.1 P, 94.18, 94.23, 8/8.57; 427/337, 339, 389

[56] References Cited

U.S. PATENT DOCUMENTS 4,018,559 4/1977 Retzsch .................................. 8/94.2

FOREIGN PATENT DOCUMENTS 0300953 11/1954 Switzerland .
1548947 4/1975 United Kingdom .

OTHER PUBLICATIONS

"Tenside als Helfsmittel zur Herstellung wasserfester Leder", Von R. Heyden, Das Leder 20, 2–8, (1969).

*Primary Examiner*—Paul Lieberman
*Assistant Examiner*—John F. McNally
*Attorney, Agent, or Firm*—Gerald D. Sharkin; Richard E. Vila; Thomas C. Doyle

[57] ABSTRACT

A method of fatting tanned leather substrates comprising
(a) applying to the substrate as the fatting agent an aqueous solution or dispersion of an ortho-phosphoric acid partial ester having attached to the phosphorus atom an average 1 to 2 (which may be a non-integral number) groups of the formula I

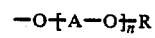

I where each A independently is

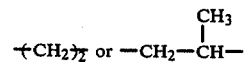

and n is a number from 2 to 10 with the proviso that 2 to 6 groups A are —(CH$_2$)$_2$,
R is an unsubstituted linear or branched (preferably linear) C$_{14-20}$alkyl group or an unsubstituted linear or branched (preferably linear) C$_{14-20}$alkenyl group,
the phosphoric acid partial ester being in free acid or salt form;
(b) treating with an agent selected from polyvalent metal oxide, hydroxide and salt, at the same time as fatting or after fatting.

28 Claims, No Drawings

USE OF PHOSPHORIC ACID PARTIAL ESTERS IN FATTING OF TANNED LEATHER

This is a continuation of application Ser. No. 722,312, filed Apr. 11, 1985, now abandoned which in turn is a continuation of application Ser. No. 410,663, filed Aug. 23, 1982, now abandoned.

The invention provides a method of fatting tanned leather substrates comprising (a) applying to the substrate as the fatting agent an aqueous solution or dispersion of an ortho-phosphoric acid partial ester having attached to the phosphorus atom an average 1 to 2 (which may be a non-integral number) groups of the formula I

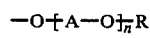     I where each A independently is

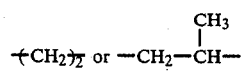

and n is a number from 2 to 10 with the proviso that 2 to 6 groups A are $-(CH_2)_2-$, R is an unsubstituted linear or branched (preferably linear) $C_{14-20}$alkyl group or an unsubstituted linear or branched (preferably linear) $C_{14-20}$alkenyl group, the phosphoric acid partial ester being in free acid or salt form; and (b) treating with an agent selected from polyvalent metal oxide, hydroxide and salt, after fatting.

When the ortho phosphoric acid partial ester is in salt form the salts are preferably alkali metal (nore preferably lithium, sodium or potassium; most preferably sodium or potassium) salts or ammonium salts (more preferably mono-, di- and trialkyl or alkano) ammonium salts; the alkyl or alkanol groups being of 1 to 4 carbon atoms.)

Preferably R is R' where R' is an alkyl or alkenyl group derived from tetradecanol, cetyl alcohol, oleyl alcohol, stearyl alcohol and tallow fat alcohol. More preferably R is R" where R" is $C_{16}$–$C_{18}$alkyl or alkenyl, most preferably $C_{16-18}$alkyl.

Preferably n is n' where n' is 2 to 6, more preferably 3 to 5.

Most preferred groups of the formula I are of the formula I'

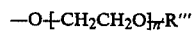     I' where R'" is cetyl or stearyl, and n' is 2 to 6.

Preferred ortho phosphoric acid partial esters are of the formula II

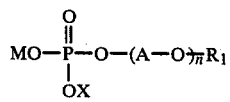     II where M is hydrogen, an alkali metal or ammonium as defined above.

X is M (above defined) or $-(A-O)_{\overline{n}}R_1$ where the symbols A and $R_1$ are defined below each $R_1$ independently is an unsubstituted $C_{14-40}$ linear or branched alkyl or a $C_{14-20}$ linear or branched alkenyl group each A independently is

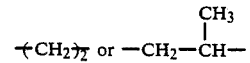

n is a number from 2 to 10 with the proviso that 2 to 6 groups A are $-(CH_2)_2-$ and mixtures thereof.

In the above formulae the indices n are average values and the groups R have an average number of carbon atoms particularly in the case where R is derived from a mixture of alcohols.

In the above compounds of formula II in which X is M preferably one of the groups X or M is hydrogen and the other is an alkali metal or ammonium group.

In order to form the salt or partial salt of compounds of formula II, the compound of formula II is preferably treated in the presence of water with a base until a pH of 5 to 8 is reached preferably 6 to 8, more preferably 6 to 7.

Preferably the phosphoric acid partial esters used in the method of the invention are water-soluble or form a dispersion in water without the aid of additional dispersing agents. By "water soluble" is meant that the esters are soluble to the extent of at least 3 g/l, preferably 10 g/l at 20° in distilled water. By the term "form a dispersion in water" is meant that on average the particle size in the dispersion is no greater than 5 μm (preferably *none* of the particles is greater than 5 μm) more preferably the particle size in the dispersion on average is no greater than 1 μm (most preferably *none* of the particles is greater than 1 μm.

In step (b) where the agent is a polyvalent metal oxide, hydroxide or salt, an example of metal oxide is MgO and of metal hydroxide is Ca(OH)$_2$. The metal salts are however preferred. Preferred cations of the agent are magnesium, calcium, barium, and more preferably aluminium, chromium (iii) and zirconyl.

Preferred agents are the water-soluble salts of the above metals, more preferably selected from aluminium sulphate, potassium chromium alum, chromium hydroxy sulphate, zirconylchloride, zirconyl sulphate, zirconyl acetate, chromium sulphate and alum.

Further, according to the invention there is provided an aqueous fatting composition comprising (i) an ortho-phosphoric acid partial ester having attached to each phosphorus atom an average 1 to 2 (which may be a non-integral number) groups of the formula I

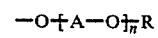     I where each A independently, is

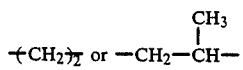

and n is a number from 2 to 10 with the proviso that 2 to 6 groups A are $-(CH_2)_2-$; and R is an unsubstituted linear or branched $C_{14-20}$alkyl group or an unsubstituted linear or branched $C_{14-20}$alkenyl group, the partialester being in free acid or salt form; and (ii) a mono- or di-ethylene glycol mono-($C_{2-8}$alkyl)ether and optionally a water soluble mono- or di-($C_{2-8}$)-alkylene glycol.

Preferred diethylene glycol monoalkyl ethers are those having $C_{5-8}$alkyl groups, more preferably $C_{7-8}$alkyl groups. Preferred monoethylene glycol monoalkyl ethers are those having $C_{2-6}$alkyl groups more preferably $C_{3-5}$alkyl groups. Of the glycol ethers of component (ii), the monoethylene glycol monoalkyl ethers are preferred.

The most preferred glycol ether of component ii is 2-n-butoxyethanol.

Preferred monoalkylene glycols of component ii are those having a $C_{2-6}$alkylene group and preferred dialkylene glycols are those having $C_{2-3}$alkylene groups. The monoalkylene glycols are more preferred to the dialkylene glycols.

Preferably the fatting compositions of the invention may include one or more further additives selected from (iii) a non-fatting hydrocarbon oil, (iv) isopropanol; and (v) up to 1% by dry weight of component (i) of an anti-foaming agent and/or a fungicide. Preferably when components (iii) and/or (iv) are present, component (ii) includes a monoalkylene glycol in the fatting composition of the invention.

Preferred non-fatting hydrocarbon oils are in general natural, semi-synthetic and synthetic hydrocarbons that are liquid at room temperature (20° C.) and have a boiling point of 250° C. and below. Preferred oils are substantially pure aliphatic or substantially aliphatic oils in particular petroleum ether (boiling point 80°–110° C.) and white spirit (b.p. 150°–250° C.). White spirit having a boiling point in the range 200°–250° C., is most preferred.

Preferred fatting compositions of the invention in aqueous solution or dispersion (with no component (iii) or (iv) above) comprise:
30–80% by weight of component (i)
4–30% by weight of component (ii)
10–66% by weight of water.

More preferably fatting compositions of the invention in aqueous solution or dispersion (with no components (iii) or (iv) above) comprise:
60–75% by weight of component (i)
5–25% by weight of component (ii)
15–35% by weight of water.

Preferred aqueous fatting compositions of the invention (including components (iii) and (iv) above) comprise:
20–55% by weight of component (i)
3–20% by weight of component (ii)
7–45% by weight of water
3.5–45% by weight of component (iii)
0–30% by weight of component (iv)
with the proviso that components (ii) and (iii) comprise at least 14% by weight of the composition.

More preferred aqueous fatting compositions of the invention (including components (iii) and (iv) above) comprise:
40–52% by weight of component (i)
4–15% by weight of component (ii)
10–24% by weight of water
8–26% by weight of component (iii)
6–20% by weight of component (iv)
with the proviso that components (ii) and (iii) comprise at least 20% by weight of the composition.

The compositions comprising components (iii) and (iv) are preferred to those not containing components (iii) and (iv).

The amount of after-treatment agent used with respect to the dry weight of phosphoric acid partial ester used is preferably 1 to 100%, more preferably 5 to 20%.

The phosphoric acid partial esters are known and may be produced according to known methods for example the reaction of poly-alkylene glycol mono ether with phosphorus pentoxide, phosphoroxy chloride or polyphosphoric acid, more preferably with phosphorus pentoxide.

The compounds of component (ii) are known and may be produced according to known methods for example by the reaction of alcohol with alkylene oxide in the presence of a catalytic amount of an alkali metal hydroxide to form the mono- or poly-alkylene glycol ethers. Components (iii), (iv) and (v) are known and may be made according to known methods.

Fatting compositions according to the invention may be formed according to known methods for example by mixing the individual components (i) and (ii) and optionally water, component (iii) component (iv) and component (v) together.

One preferred method for preparing an aqueous fatting composition of the invention containing no components (iii) and (iv) is first to oxyalkylate the $C_{14-20}$alkanol or alkenol to the required degree then treat with phosphoric acid anhydride or phosphorousloxy chloride or a polyphosphoric acid to produce the phosphoric partial ester. After this, the partial ester may be treated with an appropriate base to give the required salt at a pH of 5–8 and then the partial ester is mixed with component (ii). The addition of base alternatively may be after the addition of component (ii) and then water may be added thereafter.

A further method for preparing fatting compositions including components (iii) and (iv) comprises melting component (i) and then component (ii) is added to the melt at a temperature from 20°–100° C. Then base may be added and then isopropanol followed by component (iii) and then followed by the addition of water. The pH of the composition is preferably 5 to 8. If further additives such as antifoaming agents and fungicides are to be present these can be added as the last component to the composition.

The fatting compositions (preferably in aqueous form) according to the invention are preferably applied to leather according to known fatting methods using aqueous solutions.

For fatting leather the fatting compositions of the invention preferably containing components (iii) and (iv) may be directly added as the fatting agent. The oil containing compositions are stable to storage. One test for stability to storage is to heat the composition to 50° C. and then allow it to cool to 20° C. and then leave the composition for 24 hours at 20° C. (room temperature). The composition is stable to storage if it is not significantly changed at the end of this period.

Preferred leather substrates are those which have been tanned, for example naturally tanned leather, combined tanned or synthetically tanned leather (for example chrome tanned, zirconyl tanned, aluminium tanned leather) or leather than is re-tanned.

Preferred leather substrates are grain leather for example nappa from sheep or goat or box leather from calf or cow or cow hide or velours leathers preferably from sheep, goat or cow, and more preferably hunting leather, split velours from cow or calf skin and nubuk leather. Also fur velours may be so treated.

Optionally the leather may be dyed before treatment with the phosphoric acid partial ester. Preferred dyestuffs are those usual for dyeing leather, more preferably anionic, metal-free or metalised azo dyestuffs.

Fatting of leather may be carried out according to known methods for example exhaustion or impregnation (for example by padding, spraying or foam-treating). Exhaustion is however preferred.

Preferably the concentration of phosphoric acid partial ester (with reference to the folding weight of leather treated) is 0.2 to 15%, more preferably 2 to 8%.

The aqueous fatting bath preferably has a pH of from 2 to 9, more preferably from 4 to 7. The pH adjustment may be carried out by the addition of appropriate acid, base or buffer solution, preferably formic acid or ammonium or alkali-metal-carbonate.

The preferred temperatures for fatting leather are from 20° to 70° C., more preferably from 40° to 60° C.

The treated leather may be dried and finished according to known methods.

The treatment with metal oxide, hydroxide or salt may be applied by exhaustion or impregnation (for example padding, spraying or foam-treating). Exhaustion from aqueous medium is more preferred. The agent may be added to the fatting bath on termination of the fatting process using the same aqueous medium as is used for the fatting process.

The treatment with metal oxide, hydroxide or salt is preferably carried out at 20° to 70° C., more preferably 40° to 60° C.

The pH of the treatment is preferably 2 to 9, more preferably 4 to 7. The pH adjustment may be carried out by the addition of appropriate acid, base or buffer solution preferable formic acid or ammonium- or alkalimetal carbonate.

After treatment with the above agent, the leather may be finished according to known methods.

Leather when treated according to a fatting method according to the invention or with a fatting composition according to the invention, optionally followed by a treatment with metal oxide, hydroxide and/or salt, shows good tear resistance and hydrophobicity and is supple for instance has a good handle and has good fastness properties related to leather, in particular fastness to dry cleaning.

The invention will now be illustrated by the Examples in which all parts and percentages are by weight and all temperatures are in °C., unless indicated to the contrary.

EXAMPLE 270.5 g of stearyl alcohol and 0.5 g of pulverised sodium hydroxide are placed in a 1.5 l four-necked flask and heated to 150°. The flask is evacuated and then filled with gaseous ethylene oxide. 176 g of ethylene oxide are introduced at normal pressure and at a temperature of 150°–190°. At the end of the reaction the flask is flushed with nitrogen and cooled to 70°. 71 g of phosphorus pentoxide are added, portion by portion at 70°–80°. After the addition the reaction mixture is left to react for 6–8 hours at 75° to 80°. Then the reaction product is poured into 1645 g of 2.43% sodium hydroxide and a 25% neutral solution of the phosphoric partial ester forms.

EXAMPLE 2

In an analogous fashion to the method of Example 1, 242.5 g of cetyl alcohol is reacted with 174 g of 1,2-propyleneoxide followed by 264 g of ethylene oxide and then the mixture is reacted with 85 g of polyphosphoric acid (having a $P_2O_5$ content of 83–84%). Then the reaction product is poured into 1570 g of a 3.6% solution of potassium hydroxide to give a neutral 35% viscous paste.

EXAMPLE 3

In an analogous manner to Example 1 268 g of oleyl alcohol is ethoxylated with 132 g of ethylene oxide and then reacted with 71 g of phosphorus pentoxide. Then the reaction product is poured into 1140 g of 1.5% ammonia solution to give 1628 g of a viscous product having 30% active substance.

EXAMPLE 4

(a) In an analogous manner to Example 1, 260.4 g of tallow fat alcohol (having a hydroxyl number of 215) is ethoxylated with 167 g. of ethylene oxide and finally reacted with 71 g of phosphorus pentoxide at 50°–60° C. to form 498 g of the phosphoric half ester. (b) Alternatively, 260.4 g of tallow fat alcohol may be ethoxylated with 198 g of ethylene oxide followed by reacting with 153.5 g of phosphorus oxychloride (instead of the phosphorus pentoxide) at 40° C. followed by a 5 hour reaction at 60° C. Then the phosphoric partial ester is poured in 1500 ml of water and then neutralised with sodium hydroxide to a pH of 7.

EXAMPLE 5

Instead of pouring the phosphoric partial ester into sodium hydroxide solution, in the method of Example 1, 133 g of 2-isopropoxyethanol is added dropwise to the reaction product (at the end of the 6–8 hour period) at 50°. 68 g of a 25% ammonia solution is added and the mixture is diluted with 617 g of water to produce a paste containing 40% active substances.

EXAMPLE 6

Instead of pouring the reaction product of Example 2 into potassium hydroxide, 270 g of 2-ethoxy ethanol is poured into the reaction mixture at a temperature of 50°–60° and the product is converted to the appropriate salt by the addition of 61 g of monoethanolamine and then diluted with 310 g of water to give a 60% active substances product.

EXAMPLE 7

Instead of pouring the phosphoric partial ester into ammonia solution in Example 3, the reaction mixture is diluted with 810 g of 2-(n-hexyloxy)ethanol, reacted with 149 g of triethanolamine and finally diluted with 2066 g of water. The resultant mixture contains 30% active substances.

EXAMPLE 8

Instead of pouring the phosphoric partial ester into water followed by neutralization with NaOH in Example 4, the partial ester is diluted with 80 g of 2-(n-butoxy)ethanol and, reacted with 134.6 g of triethanolamine to give the appropriate salt and then diluted with 176 g of water. The resulting paste contains 72% active substance.

EXAMPLE 9

Instead of pouring the phosphoric partial ester into water followed by neutralization with NaOH in Example 4a the partial ester is diluted with 80 g of 2-(n-butoxy)ethanol and, reacted with 134.6 g of triethanolamine to give the appropriate salt, then diluted with 214 g of isopropanol, 145 g of water and finally 214 g of white spirit (boiling range 201°–243°).

EXAMPLES 10 TO 16

In a similar manner to the method of Example 9, the following amounts of reactants may be used, given as a percentage by weight of the total amount of reactants.

| EX. No. | Amount of phosphoric ¼ ester of Ex. 9 | Amount of glycol or 2-alkoxy alcohol | Amount of isopropanol | Amount of White Spirit as in Ex. 9 | Amount of water |
|---|---|---|---|---|---|
| 10 | 50% | 4.3% of 2-(n-butoxy)ethanol | 11.7% | 11.7% | 22.3% |
| 11 | 50% | 12.5% of 2-(n-butoxy)ethanol | 14% | 14% | 9.5% |
| 12 | 50% | 9.3% of 2-(n-butoxy)ethanol | — | 24.7% | 16% |
| 13 | 50% | 6.3% of hexylene glycol | 16.7% | 16.7% | 10.3% |
| 14 | 50% | 6.3% of 2-ethoxy ethanol | 16.7% | 16.7% | 10.3% |
| 15 | 50% | 6.3% of 2-isopropoxy ethanol | 16.7% | 16.7% | 10.3% |
| 16 | 30% | 4% of 2-butoxy-ethanol | 10% | 10% | 46% |

The products are pourable ranging from viscous to easily flowable.

In the following Application Examples A to C all percentages used are with reference to the folding weight of substrate treated unless indicated to or clearly to the contrary. The chromium hydroxy sulphate has a $Cr_2O_3$ content of 25%.

APPLICATION EXAMPLE A (Box leather from cow)

A piece of wet-blue leather is immersed in 200% water for 5 minutes at 40°. The piece is then treated for 30 minutes with 2% chromium hydroxy sulphate and 4% dimethylolethyleneurea; after which it is treated with 6% mimosa extract and 1% of the dyestuff C.I. (Colour Index) Acid Brown 359 for 1 hour and then 250% water at 40° and 0.3% of an 85% aqueous formic acid solution are added. The piece is then fatted for 45 minutes in a bath of 200% water and 20%, of the preparation of Example 1, having 5% active substance with respect to the piece treated). After this the piece is immersed for 30 minutes in 2% chromium hydroxy sulphate and 0.3% of an 85% aqueous formic acid solution. The leather is washed with 200% water at 20°, after which the leather is hung to dry overnight.

Instead of using the preparation of Example 1, any of the preparations of Examples 2–16 may be used.

APPLICATION EXAMPLE B (Hunting leather)

A wet-blue cowhide is immersed in 150% water at 30° and is tanned with 5% chromium hydroxy sulphate for 3 hours. The hide is then washed for 10 minutes with 200% water at 40°, after which the hide is immersed in a bath of pH 6.5 to 7 containing 200% water at 35° and ammonium bicarbonate. The hide is then washed with 200% water at 35° and then in a bath of 3% of the dyestuff C.I. Acid Brown 126 and 1% of a 25% ammonia solution for 45 minutes. After this, the hide is fatted by applying 23% of the preparation of Example 2 (having 8% active substances with respect to the hide) at 45° for 1 hour. The hide is then fixed by treating with 2% chromium hydroxy sulphate and 2% of an 85% aqueous formic acid solution for 30 minutes. The hide is then hung to dry overnight.

Instead of the preparation of Example 2, the preparation of Example 1, and 3 to 16 may be used in appropriate amounts.

APPLICATION EXAMPLE C (Velours from sheep)

A piece of wet-blue sheep's pelt is immersed in 800% water at 56° and 2% of a 25% aqueous solution of ammonia for 1 hour. The pelt is then tanned with 3% zirconylsulphate after which the pelt is treated with 600% water at 50° and 1% of a 25% aqueous solution of ammonia for 10 minutes. The pelt is then dyed in a bath containing 4% of the dyestuff C.I. Acid Brown 303 for 60 minutes, after which it is fatted by treating with 10% of a preparation of Example 9 (having 5% active substances with respect to the pelt) for 60 minutes. After fatting the pelt is fixed by treating with 2% chromium hydroxy sulphate and 2% of an 85% aqueous formic acid solution for 40 minutes after which the pelt is hung to dry overnight.

Instead of the preparation of Example 9 any of the preparations of Examples 1 to 8 and 10 to 16 may be used in appropriate amounts.

What is claimed is:

1. A method of fatting a tanned leather substrate comprising
   (a) applying to the substrate, as the fatting agent, an aqueous solution or dispersion of an ortho-phosphoric acid partial ester having attached to the phosphorus atom an average 1 to 2 groups of the formula I

where
R" is an unsubstituted linear or branched $C_{16-18}$ alkyl or alkenyl group, and
n is a number from 3 to 5,
the phosphoric acid partial ester being in free acid or salt form; and (b) aftertreating the thus-treated substrate with an oxide, hydroxide or a salt of a polyvalent metal selected from the group consisting of magnesium aluminum, barium, calcium, chromium (III) and zirconium.

2. A tanned leather substrate when treated according to a method of claim 1.

3. A method according to claim 1, in which in the groups of formula I, R" is cetyl or stearyl and the polyvalent metal compound is selected from aluminum sulphate, potassium chromium alum, chromium hydroxy sulphate, zirconyl chloride, zirconyl sulphate, zirconyl acetate, chromium sulphate and alum.

4. A method according to claim 1, in which the phosphoric acid partial ester is of formula II

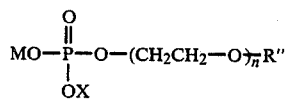

where

M is hydrogen, an alkali metal or ammonium;

X is M or $-CH_2CH_2-O)_nR''$;

and each R", independently, is an unsubstituted $C_{16-18}$ linear or branched alkyl or alkenyl group.

5. A method according to claim 1 wherein the amount of polyvalent metal oxide, hydroxide or salt is 1 to 100% of the dry weight of the phosphoric acid partial ester.

6. A method according to claim 4 wherein the amount of polyvalent metal oxide, hydroxide or salt is 1 to 100% of the dry weight of the phosphoric acid partial ester.

7. A method according to claim 4 wherein the amount of polyvalent metal oxide, hydroxide or salt is 5 to 20% of the dry weight of the phosphoric acid partial ester.

8. A method according to claim 1 wherein the phosphoric acid partial ester is present in the amount of 0.2 to 15% based on the folding weight of the leather being treated.

9. A method according to claim 4 wherein the phosphoric acid partial ester is present in an amount of 0.2 to 15% based on the folding weight of the leather being treated.

10. A method according to claim 6 wherein the phosphoric acid partial ester is present in an amount of 0.2 to 15% based on the folding weight of the leather being treated.

11. A method according to claim 7 wherein the phosphoric acid partial ester is present in an amount of 0.2 to 15% based on the folding weight of the leather being treated.

12. A method according to claim 10 wherein steps (a) and (b) are carried out at a temperature of 20° to 70° C. and at a pH of 2 to 9.

13. A method according to claim 1 wherein the ortho-phosphoric acid partial ester is the sole fatting agent applied to the substrate.

14. A method according to claim 4 wherein the ortho-phosphoric acid partial ester is the sole fatting agent applied to the substrate.

15. A method according to claim 7 wherein the ortho-phosphoric acid partial ester is the sole fatting agent applied to the substrate.

16. A method according to claim 4 wherein, in the compound of formula II, M is hydrogen, lithium, sodium, potassium, or mono-, di- or tri-$C_{1-4}$alkyl ammonium or -$C_{1-4}$alkanol ammonium.

17. A method according to claim 4 wherein, in step (b), the substrate is aftertreated with a salt selected from the group consisting of aluminum sulphate, potassium chromium alum, chromium hydroxy sulphate, zirconyl chloride, zirconyl sulphate, zirconyl acetate, chromium sulphate and alum.

18. A method according to claim 6 wherein, in the compound of formula II, M is hydrogen, lithium, sodium, potassium, or mono-, di- or tri-$C_{1-4}$alkyl ammonium or -$C_{1-4}$alkanol ammonium.

19. A method according to claim 7 wherein, in the compound of formula II, M is hydrogen, lithium, sodium, potassium, or mono-, di- or tri-$C_{1-4}$alkyl ammonium or -$C_{1-4}$alkanol ammonium.

20. A method according to claim 9 wherein, in the compound of formula II, M is hydrogen, lithium, sodium, potassium, or mono-, di- or tri-$C_{1-4}$alkyl ammonium or -$C_{1-4}$alkanol ammonium.

21. A method according to claim 10 wherein, in the compound of formula II, M is hydrogen, lithium, sodium, potassium, or mono-, di- or tri-$C_{1-4}$alkyl ammonium or -$C_{1-4}$alkanol ammonium.

22. A method according to claim 11 wherein, in the compound of formula II, M is hydrogen, lithium, sodium, potassium, or mono-, di- or tri-$C_{1-4}$alkyl ammonium or -$C_{1-4}$alkanol ammonium.

23. A method according to claim 12 wherein, in the compound of formula II, M is hydrogen, lithium, sodium, potassium, or mono-, di- or tri-$C_{1-4}$alkyl ammonium or -$C_{1-4}$alkanol ammonium.

24. A method according to claim 15 wherein, in the compound of formula II, M is hydrogen, lithium, sodium, potassium, or mono-, di- or tri-$C_{1-4}$alkyl ammonium or -$C_{1-4}$alkanol ammonium.

25. A method according to claim 20 wherein, in step (b), the substrate is aftertreated with a salt selected from the group consisting of aluminum sulphate, potassium chromium alum, chromium hydroxy sulphate, zirconyl chloride, zirconyl sulphate, zirconyl acetate, chromium sulphate and alum.

26. A method according to claim 22 wherein, in step (b), the substrate is aftertreated with a salt selected from the group consisting of aluminum sulphate, potassium chromium alum, chromium hydroxy sulphate, zirconyl chloride, zirconyl sulphate, zirconyl acetate, chromium sulphate and alum.

27. A method according to claim 23 wherein, in step (b), the substrate is aftertreated with a salt selected from the group consisting of aluminum sulphate, potassium chromium alum, chromium hydroxy sulphate, zirconyl chloride, zirconyl sulphate, zirconyl acetate, chromium sulphate and alum.

28. A method according to claim 24 wherein, in step (b), the substrate is aftertreated with a salt selected from the group consisting of aluminum sulphate, potassium chromium alum, chromium hydroxy sulphate, zirconyl chloride, zirconyl sulphate, zirconyl acetate, chromium sulphate and alum.

* * * * *